United States Patent [19]
Szymanski et al.

[11] 3,941,844
[45] Mar. 2, 1976

[54] CONTINUOUS MANUFACTURE OF N-ALKYLATED ARYLAMINES

[75] Inventors: Hans Joachim Szymanski, Schifferstadt; Toni Dockner, Meckenheim, both of Germany

[73] Assignee: BASF Aktiengesellschaft, Ludwigshafen (Rhine), Germany

[22] Filed: July 25, 1974

[21] Appl. No.: 491,626

[30] Foreign Application Priority Data
July 28, 1973 Germany............................ 2338419

[52] U.S. Cl.............. 260/577; 260/465 E; 260/571; 260/574; 260/576
[51] Int. Cl.$^2$......................................... C07C 87/62
[58] Field of Search........ 260/577, 571, 465 E, 574, 260/576

[56] References Cited
UNITED STATES PATENTS
2,115,884  5/1938  Schollkopf........................ 260/577

Primary Examiner—D. Horwitz
Attorney, Agent, or Firm—Johnston, Keil, Thompson & Shurtleff

[57] ABSTRACT

N-alkylated arylamines are prepared by reaction of arylamines which have at least one hydrogen atom on the nitrogen, with olefins or cycloolefins which can have substituents which are inert under the reaction conditions, at temperatures from 180° to 450°C, in the presence of catalysts. The improvement is that silicic acid which contains from 0.1 to 30 percent by weight of phosphoric acids, based on silicic acid, is used as the catalysts and that catalytic amounts of water are employed. N-alkylated arylamines are starting materials for the manufacture of dyes, pesticides, plant protection agents and growth regulators, and can also be used as mineral oil additives.

7 Claims, No Drawings

CONTINUOUS MANUFACTURE OF N-ALKYLATED ARYLAMINES

The invention is concerned with an improved process for the continuous manufacture of N-alkylated arylamines by reaction of arylamines with olefins or cycloolefins, which can have substituents which are inert under the reaction conditions, at temperatures from 180° to 450°C, in the presence of catalysts.

Processes for the manufacture of N-alkylated aromatic amines have already been disclosed in which aromatic amines are reacted with olefins at elevated temperature and under superatmospheric pressure, using alkali metal elements, or alkali metal hydrides or alkaline earth metal hydrides, or compounds of alkali metals with aromatic amines, as the catalysts (cf. U.S. Pat. No. 2,501,556 and German Printed Applications Nos. 1,020,984 and 1,041,505). The use of alkali metals or alkali metal hydrides or alkaline earth metal hydrides or compounds of alkali metals with amines requires that water be excluded, since otherwise the catalysts would be destroyed. Moreover, such processes are more or less unsuitable for continuous operation.

It is an object of the invention to provide a process which can very simply be carried out continuously. It is a further object of the invention to provide a process which does not have to be carried out with the exclusion of water. Yet a further object of the invention is to provide a process in which the catalysts used have a long life. Another object of the invention is to provide a process in which nuclear alkylation only occurs to a minor degree.

In accordance with the invention, these and other objects and advantages are achieved in an improved process for the manufacture of N-alkylated arylamines by reaction of arylamines which still contain at least one hydrogen atom on the nitrogen, with olefins or cycloolefins which can have substituents which are inert under the reaction conditions, at temperatures from 180° to 450°C, in the presence of catalysts, wherein the improvement is that the catalyst used is silicic acid containing from 0.1 to 30 percent by weight of phosphoric acid, based on silicic acid, and that catalytic amounts of water are co-used.

Preferably, the aromatic amines used are of the formula

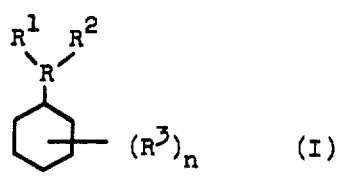

(I)

in which $R^1$ and $R^2$ are hydrogen and $R^1$ can also be alkyl of 1 to 20 carbon atoms, $R^3$ is hydrogen, nitrile or nitro, or alkyl or alkoxy with up to 4 carbon atoms or a halogen and $n$ is 1 or 2, and $R^3$ can also be phenyl or a radical of the formula

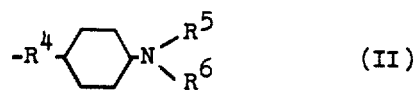

(II)

in which $R^4$ is alkylene or alkylidene of up to 3 carbon atoms and $R^4$ and $R^5$ are hydrogen and $R^5$ can also be alkyl of 1 to 20 carbon atoms, $n$ being 1.

Particularly preferred starting materials are aromatic amines which are derived from benzene and have one amino group. In addition to the amino group, the preferred aromatic amines can have 1 or 2 substituents which are inert under the reaction conditions, such as alkyl of 1 to 4 carbon atoms, alkoxy of 1 to 4 carbon atoms, nitrile, nitro or halogen such as chlorine or bromine. Starting materials which have acquired particular industrial importance are aniline or toluidines. Examples of suitable amines are aniline, o-toluidine, m-toluidine, p-toluidine, anisidines, nuclear-halogenated anilines or m- and p-nitroanilines, and also aromatic amines which contain more than one phenyl radical and carry at least one amino group on each phenyl radical, such as, for example, 4,4'-diaminodiphenylmethane and the isomeric diaminodiphenyls.

Preferably, olefins of up to 20 carbon atoms or cycloolefins of 5 to 12 carbon atoms are used. They can have substituents, preferably one substituent, which are (or is) inert under the reaction conditions, such as a phenyl group or an alkoxy group of up to 4 carbon atoms. Olefins of 2 to 10 carbon atoms or cycloolefins of 5 to 8 carbon atoms which contain an olefinic double bond and wherein the remainder of the molecule has a hydrocarbon structure are particularly preferred. Ethylene, propylene and butenes have attained particular industrial importance. Examples of suitable olefins and cycloolefins are ethylene, propylene, butylene, vinyl ethyl ether and cyclohexene.

Of course the preferred starting materials give the preferred end products.

If alkylarylamines are used as starting materials, tertiary amines are obtained. If monoalkylamines are to be produced preferentially, the preferred starting materials are primary amines but on the other hand it is also possible to recycle the monoalkylamines or dialkylamines, obtained as by-products, to the reaction, where they are alkylated further or - in the case of the dialkylarylamines are converted into monoalkylarylamines.

Advantageously, 1 to 50 moles, and in particular 5 to 30 moles, of olefins or cycloolefins are used per mole of aromatic amine.

The reaction is carried out at temperatures from 180° to 450°C. Particularly good results are obtained at temperatures from 220° to 350°C. It is advantageous to carry out the reaction under superatmospheric pressure; pressures of from 10 to 325 bars, and in particular from 100 to 300 bars, have proved suitable. Further, the reaction is carried out in the gas phase. Of course the conditions of temperature, pressure and apparatus design are so chosen that a gas phase is present.

The catalyst used is silicic acid which contains from 0.1 to 30 percent by weight of phosphoric acid, based on silicic acid. Silicic acid containing from 2 to 20 percent by weight of phosphoric acid has proved particularly suitable. The term phosphoric acid is to be understood to include ortho-phosphoric acid as well as phosphoric acids which are formed from ortho-phosphoric acid on heating. It is particularly preferred to use silicic acid of internal surface area from 5 to 500 m²/g, and especially of internal surface area from 300 to 400 m²/g. The internal surface area of the silicic acid is determined by, for example, the BET method. Suitable catalysts are obtained, for example, by the methods described in Ullmann's Enzyklopädie der technischen Chemie (Ullmann's Encyclopedia of Industrial Chemistry), 3rd edition, volume 9, pages 275 et seq. and volume 15, pages 712 et seq. An example of a particularly advantageous method of preparing suitable catalysts is to add aqueous mineral acid, for example sulfuric acid of from 20 to 35 percent strength by weight, to a sodium waterglass solution of density from 1.15 to 1.20 g/cm$^3$, convert the product, via the intermediate stage of a silicic acid sol, to a silicic acid hydrogel of high water content and wash this hydrogel with ammoniacal water, for example ammonia solution of from 0.1 to 0.2 percent strength by weight. The hydrogel thus desalinated is treated with the required amount of phosphoric acid, advantageously with the addition of oxalic acid in amounts of, for example, from 5 to 15 percent by weight based on silicic acid, in a mill or some other device which generates shear forces; this treatment causes peptization. The material thus obtained is sprayed, for example into a stream of flue gas, which gives a granular powder suitable for use as a fluidized bed catalyst, or is converted by conventional methods into a molded catalyst, for example by extrusion.

It is an essential characteristic of the invention that catalytic amounts of water are used. Particularly suitable amounts of water to be used have proved to be from 0.1 to 30 mole percent, based on aromatic amines employed.

In addition, it has proved advantageous to feed phosphoric acid and/or phosphoric acid alkyl esters continuously to the reaction. Suitable methods are to pass phosphoric acid into the catalyst bed or to vaporize phosphoric acid alkyl esters together with the starting materials used. Phosphoric acid trialkyl esters, especially with alkyl radicals of 1 to 4 carbon atoms, are preferred, and the alkyl radicals preferably correspond to the olefins used. It has proved particularly appropriate to feed from 0.1 to 5 g of phosphoric acid or phosphoric acid alkyl esters to the reaction per liter of catalyst per hour. Suitable phosphoric acid esters are trimethyl phosphate, triethyl phosphate, tripropyl phosphate or triisobutyl phosphate.

As a rule, a residence time over the catalyst of from 4 to 100 seconds is chosen. Particularly good results are also obtained by reacting from 100 to 800 g of aromatic amines per liter of catalyst and per hour.

An example of carrying out the process according to the invention is to vaporize olefins or cycloolefins with the aromatic amines described and pass the mixture over the catalyst bed of the composition described, whilst maintaining the stated temperatures and pressures. At the same time, it is advantageous to feed in phosphoric acid or phosphoric acid trialkyl esters in the amounts mentioned. Water, in the amounts mentioned, is also vaporized with the starting materials. The reaction mixture obtained is cooled and condensed, or is passed direct into a fractionating column from which the N-alkylated arylamines are obtained pure. Unconverted olefins and aromatic amines can be recycled.

N-alkylated arylamines manufactured by the process of the invention can be used as starting materials for the manufacture of dyes, pesticides or other biologically active materials, such as plant protection agents or growth regulators. They can also be used as mineral oil additives or as additives to surface coatings or other polymeric systems.

The process according to the invention is illustrated by the Examples which follow. The parts mentioned in the Examples are by weight and bear the same relationship to parts by volume as the gram to the liter.

EXAMPLE 1

Glass Raschig rings are placed in the upper part of a vertical stainless steel high pressure tube of 30 mm diameter and 2 m length, and a silicic acid catalyst which has an internal surface area of 400 m$^2$/g, contains 20 percent by weight of phosphoric acid and has been molded into 4 mm diameter extrusions is used to fill the lower part of the tube, which has a capacity of 0.4 l. A mixture of 100 g of aniline, 5 g of water, 0.5 g of triethyl phosphate and 850 liters (S.T.P.) of ethylene is passed hourly into the top of the tube. Liquid starting materials which vaporize in the upper part of the tube, and gaseous starting materials, pass as a gas over the catalyst. The temperature in the catalyst bed is 330°C and the pressure is 200 bars. The molar ratio of aniline to ethylene is 1:35. The condensate obtained hourly weighs 107 grams and contains small amounts of ethanol and water, 68.5 grams of N-ethylaniline, 23 grams of N,N-diethylaniline and 10 grams of aniline. This corresponds to 90% conversion. The yield of N-alkylated anilines is 74.5%.

EXAMPLE 2

The procedure described in Example 1 is followed except that 100 parts of aniline, 5 parts of water, 0.5 part of triethyl phosphate and 1,200 parts by volume (S.T.P.) of ethylene are passed over the catalyst per hour. The temperature in the catalyst bed is 330°C and the pressure is 300 bars.

49 parts of N-ethylaniline, 73 parts of N,N-diethylaniline and 4 parts of unconverted aniline are obtained. This corresponds to 96% conversion and to a yield of ethylated anilines of 87% of theory. After using the catalyst for 1,000 hours, the conversion and yield are unchanged.

EXAMPLE 3

The procedure described in Example 1 is followed except that 500 parts of N-ethylaniline, 5 parts of water, 2 parts of triethyl phosphate and 600 parts by volume (S.T.P.) of ethylene are used and passed over the catalyst at 300°C and 200 bars.

The condensate contains 22.5 parts of N-ethylaniline, 25.7 parts of N,N-diethylaniline and 0.6 part of aniline. The conversion is 55%. 76% of the unconverted N-ethylaniline are converted to N,N-diethylaniline. 3% are decomposed to aniline.

EXAMPLE 4

The procedure described in Example 1 is followed except that 100 parts of o-toluidine, 6 parts of water, 1 part of triethyl phosphate and 630 parts by volume (S.T.P.) of ethylene are used. The mixture is passed over the catalyst at 300°C and 200 bars.

The condensate obtained contains 14 parts of unconverted o-toluidine, 78 parts of N-ethyl-o-toluidine and 20 parts of N,N-diethyl-o-toluidine. The conversion is 86%.

72% of the unconverted o-toluidine are converted to N-ethyl-o-toluidine and 9.5% are converted to N,N-diethyl-o-toluidine.

The space-time yield of the N-alkylated o-toluidines is 190 g per liter of catalyst per hour.

Comparative Example

The procedure described in Example 1 is followed except that 100 parts of aniline without water are used and the reaction mixture is passed over the catalyst at 300° and 200 bars. (Molar ratio of aniline to ethylene = 1:30).

The condensate contains 98 parts of unconverted aniline, 1.8 parts of N-ethylaniline and small amounts of N,N-diethylaniline and nuclear-alkylated derivatives.

We claim:

1. An improved process for the continuous manufacture of N-alkylated arylamines by reaction of arylamines which have at least one hydrogen atom on the nitrogen, with olefins having 2–10 carbon atoms or cycloolefins having 5 to 8 carbon atoms, which can have substituents which are inert under the reaction conditions, at temperatures from 180° to 450°C, in the presence of catalysts, wherein the improvement comprises using silicic acid which contains from 0.1 to 30 percent by weight of phosphoric acid, based on silicic acid, as the catalyst and catalytic amounts of water of 0.1 to 30 mole percent, based on the arylamine, and feeding phosphoric acid or a phosphoric acid alkyl ester continuously to the catalyst during the reaction.

2. A process as claimed in claim 1, wherein the reaction is carried out under a pressure of from 10 to 400 bars.

3. A process as claimed in claim 1, wherein silicic acid having an internal surface area of from 5 to 500 $m^2/g$ is used.

4. A process as claimed in claim 1, wherein aromatic amines which are derived from benzene and have one amino group and can in addition to the amino group contain from 1 to 2 alkyl radicals of 1 to 4 carbon atoms, alkoxy radicals of 1 to 4 carbon atoms, nitrile or nitro groups are used as starting materials.

5. A process as claimed in claim 1, wherein aniline or toluidines are used as starting materials.

6. A process as claimed in claim 1, wherein said olefins have one olefinic double bond and wherein the remainder of the molecule has a hydrocarbon structure.

7. A process as claimed in claim 1, wherein ethylene, propylene or butenes are used as starting materials.

* * * * *